United States Patent [19]

Strom

[11] 4,348,265

[45] Sep. 7, 1982

[54] PROCESS FOR THE SELECTIVE ALIPHATIC CHLORINATION OF ALKYLBENZENES

[75] Inventor: Robert M. Strom, Midland, Mich.

[73] Assignee: The Dow Chemical Company, Midland, Mich.

[21] Appl. No.: 248,599

[22] Filed: Mar. 27, 1981

[51] Int. Cl.$^3$ .................. B01J 19/12; C07C 17/12
[52] U.S. Cl. .................. 204/158 HA; 204/163 R; 570/197
[58] Field of Search .................. 204/158 HA, 163 R; 570/196, 197

[56] References Cited

U.S. PATENT DOCUMENTS

| | | | |
|---|---|---|---|
| 2,193,823 | 3/1940 | Lavine et al. | 570/196 |
| 3,251,887 | 5/1966 | Huyser | 204/158 HA |
| 4,133,837 | 1/1979 | Markley | 204/163 R |

Primary Examiner—Howard S. Williams

[57] ABSTRACT

Alpha-chlorinated cumene derivatives are prepared by chlorinating cumene derivatives in the presence of light. The chlorination may be taken to 100 percent conversion when performed in a solvent, e.g., m-dichlorobenzene.

12 Claims, No Drawings

PROCESS FOR THE SELECTIVE ALIPHATIC CHLORINATION OF ALKYLBENZENES

BACKGROUND OF THE INVENTION

This invention relates to the selective aliphatic halogenation of the α carbon of alkylbenzenes and their aromatically-substituted derivatives. More specifically, it relates to the α-chlorination of aromatically-substituted derivatives of cumene.

It is known that halogenation of an aliphatic hydrocarbon moiety is most often a free radical process initiated by light or a free radical initiator. Generally, halogenation of aliphatic hydrocarbons is a poor method of synthesis because substitution of the halogen is largely indiscriminate. For example, in the chlorination of ethylbenzene or longer-chain alkylbenzenes, both α and β chlorination occur because disubstitution rates are nearly equal to monosubstitution rates. Bromination of higher alkyl side chains is more selective than an analogous chlorination and, therefore, yields a larger proportion of α-substituted products. Alternatively, selective halogenation of the α carbon can be increased by supplying a large excess of the alkylbenzene. Unfortunately, this excess lowers the conversion of the alkylbenzene to the α-halogenated product. See, e.g., *Survey of Organic Syntheses*, Vol. I, C. A. Buehler and D. E. Pearson (1970). As a result of the aforementioned indiscriminate substitution, prior methods of selectively halogenating the aliphatic chains of alkylbenzenes required alkylbenzene recycle streams for the excess hydrocarbon, and required expensive separation steps due to the low conversion to product.

In U.S. Pat. No. 2,193,823, a method is taught for low yield α-chlorination of ethylpentachlorobenzene by contacting the same in the liquid phase at elevated temperature with chlorine gas in the presence of the light of an ordinary electric light bulb to produce α-chloroethylpentachlorobenzene. The desired product must be separated from the reaction mixture by treating the mixture chemically to remove residual chlorine, followed by two vacuum distillation steps.

In U.S. Pat. No. 4,133,837, the preferential aliphatic halogenation (excluding chlorination) of one or more isomers in a mixture of ar-substituted alkylbenzenes was disclosed. Heating the crude product mixture under vacuum is taught as a method of separating out the chlorobenzene solvent.

Heretofore, a process for the selective chlorination of the α carbon of an alkyl side chain of an aromatically-substituted cumene derivative has not been disclosed.

SUMMARY OF THE INVENTION

The present invention is a process for the preparation of an α-chloro cumene derivative. The process comprises adding a chlorinating agent to a cumene derivative, as defined hereinafter, in the presence of a free radical initiator and under conditions sufficient to preferentially chlorinate the α position of the alkyl substituent. This preferential chlorination is surprising in that it occurs only at the α position of essentially all of the alkyl moieties of the cumene derivative, while essentially none of the ring carbons or β positions of the alkyl substituent are chlorinated. Of particular interest in the practice of this invention is the use of an inert organic solvent which allows the chlorination to be taken to substantially 100 percent conversion without product solidification, thereby obviating the need for starting material recycle streams or the costly separation of unreacted starting material from the product. Surprisingly, when the process is conducted in the presence of an appropriate solvent, essentially complete conversion of the cumene derivative to its chlorinated analogs is obtained without a substantial reduction in selectivity of α-chlorination. The α-chlorinated cumene product is useful as an intermediate in the manufacture of herbicides and other biologically active chemicals.

DETAILED DESCRIPTION OF THE INVENTION

In the practice of the present invention it is essential to employ a cumene derivative, a chlorinating agent, and a free radical initiator. A solvent is optionally employed.

Advantageously, cumene derivatives are represented by Formula I

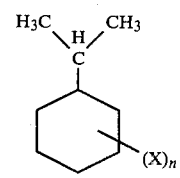

wherein X is a halogen, or any electron-withdrawing group which does not react with chlorine, such as —CF$_3$, —CCl$_3$ or —NO$_2$; and n is an integer from 1 to 5. Preferably, X is chlorine and n is 2. The most preferred cumene derivative is 3,5-dichlorocumene and it can be prepared in any number of ways. One method is disclosed in U.S. Pat. No. 4,104,315.

A suitable halogen or any agent that is capable of generating a chlorine atom, such as a suitable chlorine-containing solid or liquid, can be used as the chlorinating agent. Chlorine is the most preferred chlorinating agent. Chlorine atoms are preferably supplied at a ratio of from about 0.5 to about 1.1 moles of chlorine atoms per mole of cumene derivative. While excess chlorinating agent can be employed, too large an excess, for example greater than about 1.5 moles of chlorine atoms per mole of cumene derivative, may lead to some chlorination of the β carbon(s), as discussed hereinbefore.

Suitable free radical initiators include ultraviolet light and catalysts, such as peroxides. In the case of a peroxide, a sufficient quantity is used to cause halogenation of the α carbon. If a peroxide such as benzoyl peroxide is used, it is conveniently added to the reactants along with an optional solvent as hereinafter described. If employed, the peroxide is used in an amount between about 0.005 and about 0.05 moles of peroxide per mole of cumene derivative.

The process of this invention is suitably conducted neat or in an inert organic solvent. Preferably, it is conducted in a chlorinated aromatic solvent, especially the dichlorobenzenes, most preferably, it is conducted in m-dichlorobenzene. For the purposes of this invention, an inert solvent is a solvent which does not interfere with the selective α-chlorination of the cumene derivative being used. When solvent is employed, it is used in amounts such that the resultant product does not precipitate from solution, preferably from about 0.25 to about 0.8 moles of solvent per mole of cumene derivative. When no solvent is employed, the product crystallizes before complete conversion is reached. Thus, in a solventless system, crystallized product must be removed in order to obtain essentially complete conversion.

The selective, aliphatic chlorination step is advantageously conducted in the liquid phase at a temperature of between about 0° C. and 30° C., and preferably between about 4° C. and 15° C. The chlorination step is preferably conducted in the presence of mild agitation sufficient to maintain an essentially homogeneous mixture of the reactants.

In conducting the chlorination step, neither the rate of chlorine addition nor the order of addition of the reactants is critical provided that at any time during the reaction, no more than about 0.05 mole of chlorinating agent is present per mole of cumene derivative. A typical chlorination step generally requires from about 1 hour to about 2 hours.

The selective, aliphatic chlorination of a cumene derivative can be taken to essentially complete conversion when conducted in the appropriate solvent to yield the α-chlorinated cumene derivative. This obviates the need to separate the product from the initial reactants. The product is separable from the aromatic solvent by known crystallization techniques.

The instant reaction method requires no more time than similar prior methods. Generally speaking, however, the rate of conversion for a reaction of this type decreases as reaction temperature decreases. Therefore, it is surprising that the instant method is not more time consuming yet proceeds at a lower temperature than prior methods.

For the purposes of this invention, conversion refers to the elimination of the cumene derivative from the reaction mixture. For example, in the practice of this invention, 3,5-dichlorocumene is essentially completely converted to the compounds listed in Example 1. At essentially complete conversion of the reactant in the practice of this invention, the reaction is considered to be selective if at least 80 mole percent of the cumene derivative is converted to the α-chloro cumene derivative and/or its dehydrohalogenated analogue, preferably at least 90 mole percent, most preferably at least 92 mole percent.

The following examples are given to illustrate the invention and should not be construed as limiting its scope. All percentages in the examples are by weight unless otherwise indicated.

EXAMPLE 1

In a 300-milliliter vessel equipped with a dip tube, a stirring means and a cooling means, a mixture is formed by adding to the vessel with stirring 73 g of 3,5-dichlorocumene and 32 g of m-dichlorobenzene. The mixture is cooled to 5° C. and is then stirred while simultaneously being sparged with gaseous nitrogen for 15 minutes. A 275 watt mercury vapor/incandescent lamp is placed about 1 inch from the vessel. Gaseous chlorine is then introduced at approximately one gram per minute through the dip tube.

The mixture is analyzed periodically using gas chromatography, and chlorine addition is stopped when 3,5-dichlorocumene no longer can be detected. At this point 28 minutes have elapsed since chlorine addition started. Yields are determined by dehydrochlorination of the α-chloro-3,5-dichlorocumene followed by comparison with authentic 3,5-dichloro-α-methylstyrene. The yield of α-chloro-3,5-dichlorocumene is about 92 mole percent, including that which is present as 3,5-dichloro-α-methylstyrene, and no solids are observed. This indicates high correlation between conversion to the α-chloro product and selectivity, because conversion is approximately 100 percent and selectivity is 92 percent from 3,5-dichlorocumene to α-chloro-3,5-dichlorocumene, including that present as 3,5-dichloro-α-methylstyrene. The final reaction mixture contains 3,5-dichloro-α-methylstyrene, α-chloro-3,5-dichlorocumene, β-chloro-3,5-dichlorocumene, and α,β-dichloro-3,5-dichlorocumene.

EXAMPLE 2

The procedure of the first example is followed except that no m-dichlorobenzene (solvent) is employed, and the mass of 3,5-dichlorocumene is increased to 277 g. The 3,5-dichlorocumene is added to the vessel first. Gaseous chlorine is then introduced at approximately one gram per minute. The temperature of the vessel is maintained at 6° C. The vessel contents solidify when 100 g of chlorine has been added. No further chlorine is added. The vessel contains about 77.5 percent α-chloro-3,5-dichlorocumene, about 11 percent 3,5-dichlorocumene, about 2 percent 3,5-dichloro-α-methylstyrene, and about 5.5 percent β- and α,β-chlorinated-3,5-dichlorocumene.

The lack of a solvent causes the 3,5-dichlorocumene reaction mixture to solidify before complete conversion is attained.

Following the procedure of the first example and using the apparatus described therein, 55 g of 3,5-dichlorocumene and 100 ml of 1,2-dichlorotetrafluoroethane are added to the vessel. Analysis by gas chromatography shows that no 3,5-dichlorocumene is present 23 minutes after chlorine is first added. Further, the analysis shows the yield of α-chloro-3,5-dichlorocumene to be 71.6 mole percent, indicating a lack of selectivity to the α position.

This comparative experiment shows that 1,2-dichlorotetrafluoroethane is not an inert organic solvent for the purposes of this invention because it interferes with the selective α-chlorination of 3,5-dichlorocumene.

What is claimed is:

1. A process for the preparation of α-chlorinated cumene derivatives, which comprises contacting a chlorinating agent with a cumene derivative represented by formula I

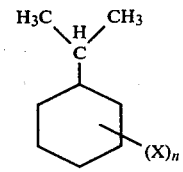

wherein n is a whole number from 1 to 5, and X is a halogen or any electron-withdrawing group which does not react with chlorine, in the presence of a free radical initiator and under conditions sufficient to selectively chlorinate the α carbon of the isopropyl side chain of the cumene derivative, and under such conditions that at least 80 mole percent of the cumene derivative is converted to the corresponding α-chlorocumene derivative or its dehydrochlorinated analogue.

2. The process of claim 1 wherein the free radical initiator is ultraviolet light.

3. The process of claim 2 wherein the chlorinating agent is chlorine and the process is conducted at a temperature between about 4° C. and about 15° C.

4. The process of claim 3 further comprising the use of an aromatic solvent; and wherein the ratio of moles of chlorine atoms to moles of cumene derivative is from about 0.5 to about 1.1, with the proviso that no more than about 0.05 mole of chlorine is present at any point in time per mole of cumene derivative.

5. The process of claim 4 wherein the aromatic solvent is m-dichlorobenzene.

6. The process of claim 5 wherein the cumene derivative has one X group in either the 3 or 4 position on the ring.

7. The process of claim 5 wherein X is chlorine and n is 2.

8. The process of claim 7 wherein the cumene derivative is 3,5-dichlorocumene and the resultant product is α-chloro-3,5-dichlorocumene.

9. The process of claim 8 wherein greater than 92 mole percent of the 3,5-dichlorocumene is converted to α-chloro-3,5-dichlorocumene or 3,5-dichloro-α-methylstyrene.

10. The process of claim 1 wherein the chlorinating agent is chlorine.

11. The process of claim 1 wherein the process is conducted at a temperature between about 0° C. and about 30° C.

12. The process of claim 1 further comprising the use of an inert organic solvent.

* * * * *

UNITED STATES PATENT AND TRADEMARK OFFICE
CERTIFICATE OF CORRECTION

PATENT NO. : 4,348,265
DATED : September 7, 1982
INVENTOR(S) : Robert M. Strom

It is certified that error appears in the above—identified patent and that said Letters Patent is hereby corrected as shown below:

Column 2, Formula I which includes lines 20-26 which now reads

"  " should read --  --.

Column 4, lines 29 & 30, a new paragraph was deleted and should be inserted between these lines -- Comparative Experiment (Not an example of this invention) --.

Column 4, Formula I which includes lines 50-56 which now reads

"  " should read --  --.

Signed and Sealed this

First Day of March 1983

[SEAL]

Attest:

GERALD J. MOSSINGHOFF

Attesting Officer   Commissioner of Patents and Trademarks